United States Patent
Heitmann

(10) Patent No.: US 9,457,384 B2
(45) Date of Patent: Oct. 4, 2016

(54) AUTOMATIC RINSING MACHINE, IN PARTICULAR AN AUTOMATIC DISINFECTION MACHINE, AN ENDOSCOPE RINSING MACHINE AND/OR THE LIKE

(71) Applicant: Miele & Cie. KG, Guetersloh (DE)

(72) Inventor: Michael Heitmann, Bielefeld (DE)

(73) Assignee: MIELE & CIE. KG, Guetersloh (DE)

(*) Notice: Subject to any disclaimer, the term of this patent is extended or adjusted under 35 U.S.C. 154(b) by 0 days.

(21) Appl. No.: 14/817,216

(22) Filed: Aug. 4, 2015

(65) Prior Publication Data
US 2016/0045939 A1 Feb. 18, 2016

(30) Foreign Application Priority Data
Aug. 18, 2014 (DE) .................. 10 2014 111 718

(51) Int. Cl.
*B08B 3/04* (2006.01)
*A47L 15/00* (2006.01)
*A47L 15/42* (2006.01)
*A61L 2/24* (2006.01)

(52) U.S. Cl.
CPC .............. *B08B 3/04* (2013.01); *A47L 15/0081* (2013.01); *A47L 15/4257* (2013.01); *A61L 2/24* (2013.01); *A61L 2202/121* (2013.01); *A61L 2202/122* (2013.01); *A61L 2202/24* (2013.01)

(58) Field of Classification Search
CPC .............. A47L 15/4261; D06F 39/14; E05Y 2900/304; E05F 1/1276; F24C 15/023
USPC ...... 134/165, 58 DL, 181, 56 R, 57 D, 57 R, 134/58 D; 16/48.5, 82, 412, 49, 61, 96 R; 49/506, 280, 358, 139, 140, 158, 18; 312/319.2, 228, 229, 272, 312
See application file for complete search history.

(56) References Cited

FOREIGN PATENT DOCUMENTS

| DE | 19514303 A1 | * 10/1996 | .......... A47L 15/0081 |
|---|---|---|---|
| DE | EP 2604296 | * 12/2011 | ............ A47L 15/42 |
| EP | 0859197 A2 | 8/1998 | |
| EP | 1333118 A1 | 8/2003 | |
| EP | 1949843 A1 | 7/2008 | |
| EP | 2604296 A1 | 6/2013 | |
| IT | EP 1949843 A1 | * 7/2008 | .......... A47L 15/0081 |

(Continued)

OTHER PUBLICATIONS

Fiedler, Kurt, "Washing Machine for laboratory or hospital" Oct. 1996, DE 19514303—Machine Translation.*

(Continued)

*Primary Examiner* — David Cormier
*Assistant Examiner* — Thomas Bucci
(74) *Attorney, Agent, or Firm* — Leydig, Voit & Mayer, Ltd.

(57) ABSTRACT

An automatic rinsing machine includes a rinsing container with a lifting door and a rinsing chamber with a rinsing chamber opening closed in a fluid-tight manner by the lifting door. A drive device displaces the lifting door. The drive device includes a load-bearing tension unit. A lever arrangement is disposed between the load-bearing tension unit and the lifting door. The lever arrangement includes a clamping device that is guided in parallel with a direction of movement of the lifting door. The lifting door and the clamping device are supported under spring preload with respect to a common abutment.

8 Claims, 3 Drawing Sheets

(56) References Cited

FOREIGN PATENT DOCUMENTS

| | | |
|---|---|---|
| JP | 2012050580 A | 3/2012 |
| WO | WO 0211602 A2 | 2/2002 |

OTHER PUBLICATIONS

Heitmann, Michael, "Automatic Washing Machine" Dec. 2011, EP 2604296—Machine Translation.*

* cited by examiner

AUTOMATIC RINSING MACHINE, IN PARTICULAR AN AUTOMATIC DISINFECTION MACHINE, AN ENDOSCOPE RINSING MACHINE AND/OR THE LIKE

CROSS-REFERENCE TO PRIOR APPLICATION

Priority is claimed to German Patent Application No. DE 10 2014 111 718.2, filed on Aug. 18, 2014, the entire disclosure of which is hereby incorporated by reference herein.

FIELD

The invention relates to an automatic rinsing machine, in particular to an automatic disinfection machine, to an endoscope rinsing machine and/or the like, comprising a rinsing container which has a rinsing chamber with a rinsing chamber opening which can be closed in a fluid-tight manner by a lifting door, and comprising a drive device for motorized displacement of the lifting door, the drive device having a load-bearing tension unit.

BACKGROUND

An automatic rinsing machine is known from EP 2 604 296 A1.

The previously known automatic rinsing machine has a rinsing container which, for its part, provides a rinsing chamber for receiving items to be rinsed to be cleaned and/or disinfected. The rinsing chamber has an opening for loading items to be rinsed to be cleaned and/or disinfected into the rinsing chamber. This opening can be closed in a fluid-tight manner by a lifting door.

The lifting door can be moved in the elevation direction of the automatic rinsing machine. Said door is preferably moved in a motorized manner, for which a drive device is provided. Said drive device has a load-bearing tension unit which is coupled to the lifting door. In the construction previously known from EP 2 604 296 A1, a toothed belt is used as the tension unit.

For increased operational reliability, the automatic rinsing machine according to EP 2 604 296 A1 has a mechanical lock which engages if the tension unit fails, for example due to tearing. For this purpose, the automatic rinsing machine has a locking device which has on one hand a locking lever and on the other an abutment provided with recesses. If the tension unit tears, the spring-pretensioned locking lever of the locking device pivots out and engages in a recess in the abutment, as a result of which the lifting door is locked mechanically. Consequently, when activated, the locking device secures the position of the lifting door, whereby the lifting door is reliably prevented from falling down in an uncontrolled manner.

Although the locking device of the previously known automatic rinsing machines has proved effective in everyday practical use, it is not free from disadvantages. Thus, the construction of the mechanical lock means that the braking effect only takes place during the passage over a recess, provided for this purpose in the abutment. Furthermore, the braking effect occurs suddenly when locking in, which leads to a considerable force being applied to the abutment and is also associated with corresponding noise generation.

SUMMARY

An automatic rinsing machine includes a rinsing container with a lifting door and a rinsing chamber with a rinsing chamber opening closed in a fluid-tight manner by the lifting door. A drive device displaces the lifting door. The drive device includes a load-bearing tension unit. A lever arrangement is disposed between the load-bearing tension unit and the lifting door. The lever arrangement includes a clamping device that is guided in parallel with a direction of movement of the lifting door. The lifting door and the clamping device are supported under spring preload with respect to a common abutment.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
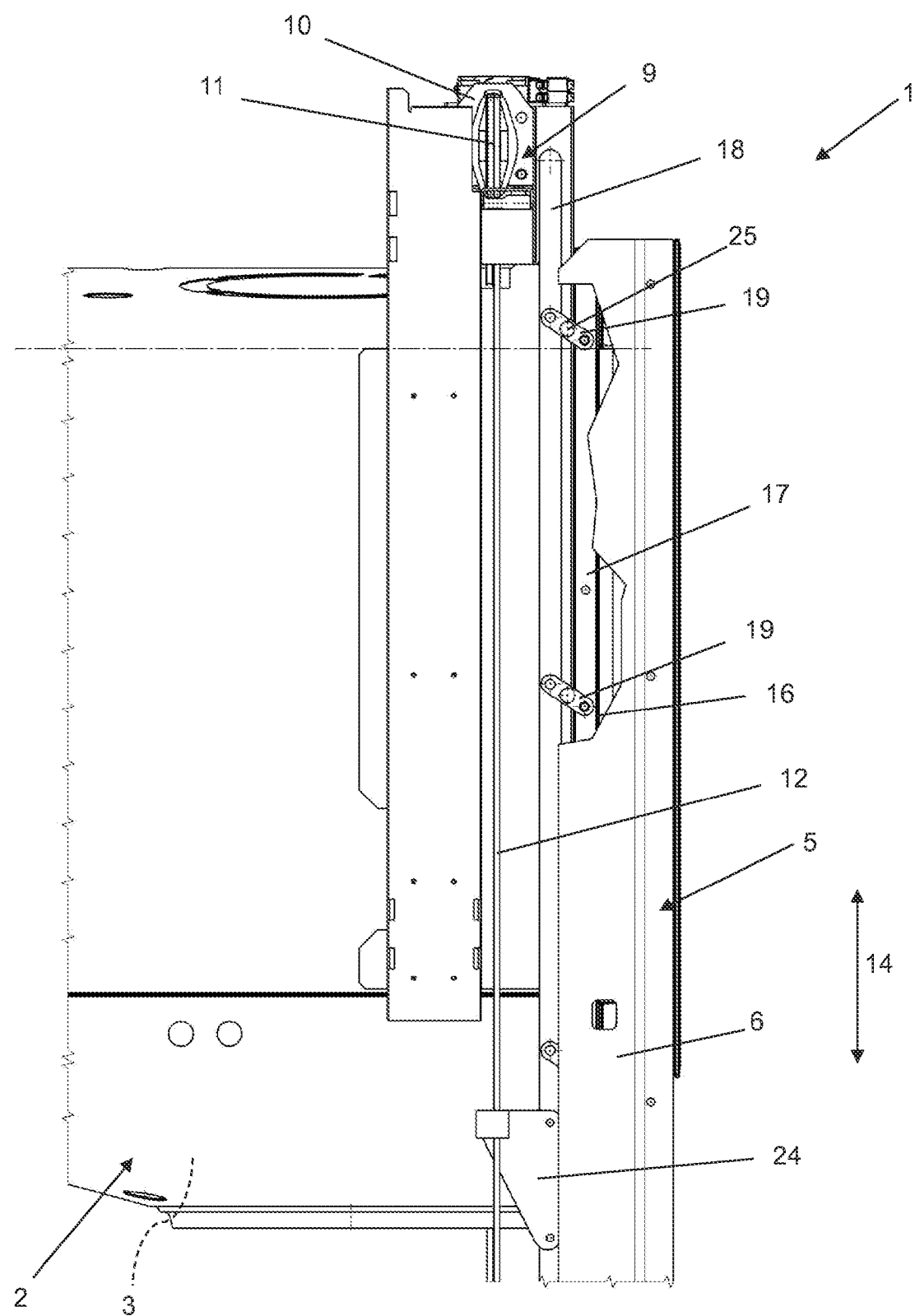
FIG. 1 is a schematic side view of a detail of the automatic rinsing machine according to the invention.

In an embodiment, the present invention provides an automatic rinsing machine of the type mentioned at the outset which is distinguished by a lever arrangement which is disposed between the tension unit and the lifting door and has a clamping device guided in parallel with a direction of movement of the lifting door, the lifting door and the clamping device being supported under spring preload with respect to a common abutment.

In contrast to the prior art, the load-bearing tension unit, for example a toothed belt or a cable, is not arranged directly on the lifting door, but with the interposition of a lever arrangement. The lever arrangement has a clamping device which is guided in parallel with a direction of movement of the lifting door. The lifting door and the clamping device are spring-preloaded by an appropriate tension spring and are supported on a common abutment. If the lifting door falls down, this spring preload ensures that the lifting door and the clamping device rest against the abutment in a friction-locking manner, which stops the lifting door. In contrast to the prior art, the configuration according to the invention produces a friction-locking, instead of a form-locking, braking and stopping of the lifting door. Unlike the prior art, this friction-locking braking engages immediately and not only after the passage over a locking point. The braking is thereby softer and relatively gentle on materials.

A further effect of the construction according to the invention is that during displacement, the lifting door is initially raised from the associated seal of the rinsing chamber opening so that damage to the seal due to the lifting door sticking is avoided.

If the rinsing chamber door is raised during intended use, the weight of the lifting door compresses the tension spring causing the spring preload. In this respect, the lever arrangement performs a swivelling movement and lifts the rinsing chamber door from the associated seal of the rinsing chamber door opening. Consequently, the lifting door can move freely and can be displaced in the elevation direction. If the force-locking connection is then interrupted, the spring force, released thereby, of the tension spring presses the lifting door against the seal. The friction arising thereby between the lifting door and the seal intensifies the spring force and thereby the pressing-on action of the lifting door so that, in turn, the friction force increases and ultimately becomes greater than the weight so that the lifting door is arrested.

A further feature of the invention provides that the clamping device is a clamping strip. This strip is arranged in a vertically extending guide. Thus during intended use, the clamping strip is guided in the elevation direction of the automatic rinsing machine. The length of the clamping strip is selected such that during operation, the clamping strip and the lifting door are pressed securely against the abutment, so that the lifting door can be braked and arrested with the development of the frictional lock which then prevails.

According to a further feature of the invention, the tension unit is connected to a tension rod which is guided in parallel with the clamping device. The tension rod itself is flange-mounted on the lifting door so that during intended use, a force is introduced into the lifting door with the interconnection of the tension rod.

A further feature of the invention provides that the lever arrangement has a swivelling lever which at one end is arranged such that it can swivel on the tension rod and at the other end is arranged such that it can swivel on the clamping device. In this manner during intended use, a parallel movement of the tension rod and clamping device is achieved which entails a particular disengaging movement, which advantageously leads to the lifting door being raised from the seal of the rinsing chamber opening. Redundant mechanical stresses on the seal can thereby be avoided, which increases the service life of the seal.

A stop is preferably provided which restricts the swivelling of the swivelling lever. This stop prevents the lifting door from performing an excessive outward movement, i.e. from being raised too far from the seal of the rinsing chamber opening and thereby colliding with trim parts when it is subsequently opened. Furthermore, the clamping lever is prevented from swivelling into a vertical extended position from which it would no longer swivel back during the subsequent closure of the lifting door. In addition, the spring element, i.e. for example the tension spring, is protected against overextension. The stop is advantageously arranged on the clamping device, in particular on the clamping strip.

According to a further feature of the invention, the swivelling lever is rotatably arranged on the lifting door. Thus, a force is introduced into the lifting door from the tension rod via the swivelling lever.

A further feature of the invention provides that the lifting door has a door frame which supports the swivelling lever on the inside such that it can rotate thereon. In this manner, a compact arrangement of the swivelling lever is obtained which cannot be seen by the user when viewing the automatic rinsing machine from the front.

According to a further feature of the invention, four swivelling levers are provided on each side of the door frame. This ensures that even when the lifting door is in the open position, at least two swivelling levers still ensure that the clamping strip and of the lifting door press against the associated abutment in the manner intended.

In contrast to the prior art, the configuration according to the invention provides a clamping device preferably configured as a clamping strip which provides frictional automatic locking during interaction with the lifting door. This automatic locking engages relatively silently and also allows for continuous positional fixing of the lifting door. In this respect, the frictional automatic locking takes place according to the invention in that a clamping strip guided in parallel with the lifting door is provided. This strip is pushed away in a spring-loaded manner from the lifting door or, in the event of a breakdown, they are guided towards one another which results in the automatic locking and thereby in an emergency braking during interaction with the abutment provided for this purpose. In this respect, the emergency braking always advantageously engages, whatever the nature of the breakdown, when the tension rod coupled to the clamping strip is rendered ineffective. In this respect, the automatic locking according to the invention not only engages if the tension unit, for example the cable, tears, but also if a drive, a transmission and/or the like is defective.

Figure 2:
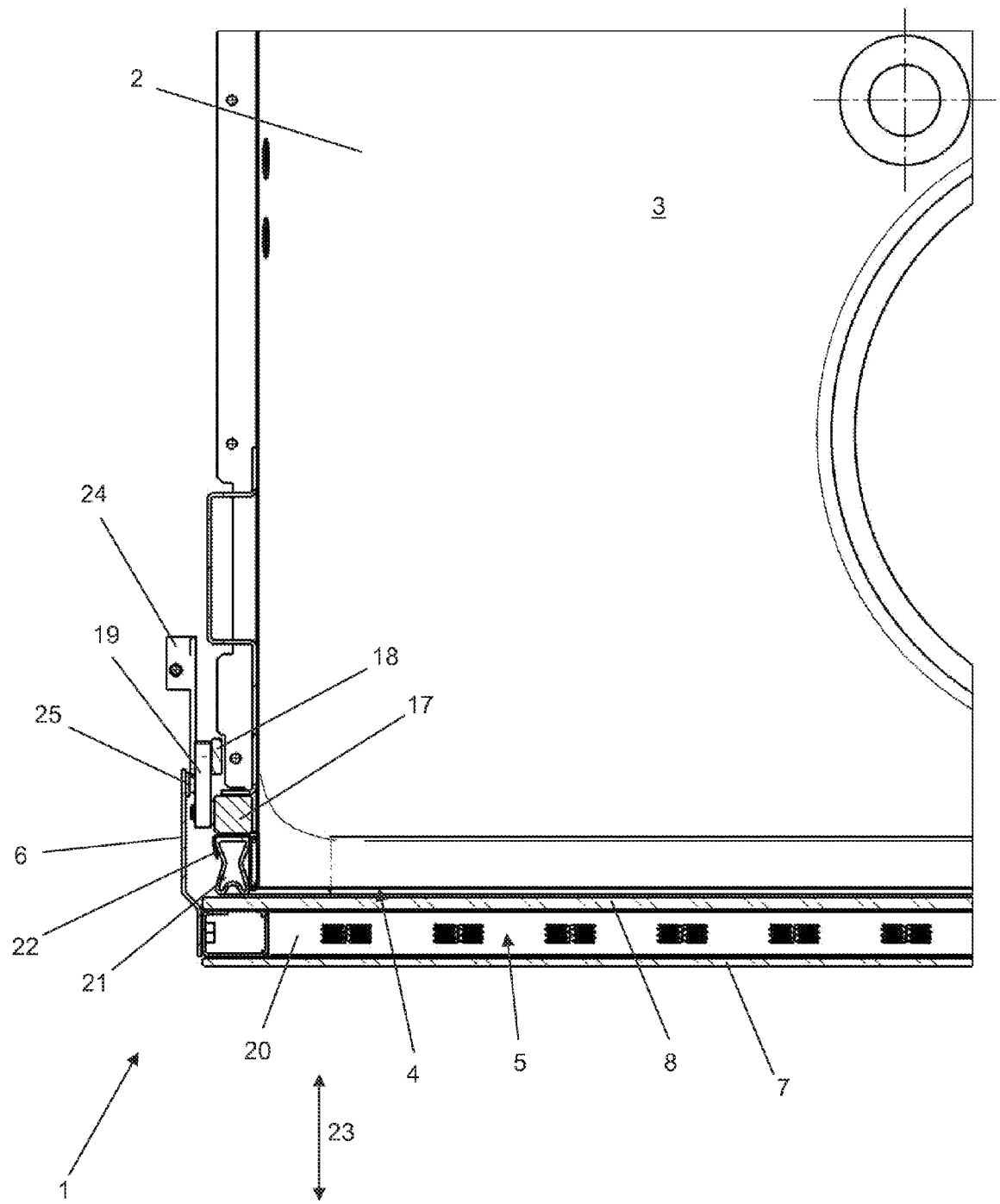
FIG. 2 is a plan view from above of a detail of the automatic rinsing machine according to the invention of FIG. 1.

FIGS. 1 and 2 show details of the automatic rinsing machine 1 according to the invention, more specifically in a side view according to FIG. 1 and in a plan view from above according to FIG. 2.

As can be seen from looking at both FIGS. 1 and 2, the automatic rinsing machine has, in a manner known per se, a rinsing container 2 which provides a rinsing chamber 3. The rinsing chamber 3 is accessible via a rinsing chamber opening 4, said rinsing chamber opening 4 being closable in a fluid-tight manner by a lifting door 5. In this respect, the lifting door 5 is configured to be movable in the direction of movement 14, i.e. in the elevation direction of the automatic rinsing machine 1.

The lifting door 5 provides an outer pane 7 and an inner pane 8 which are arranged at a distance from one another with the interposition of a profile frame 20. A door frame 6 serves to arrange the lifting door 5 on the rinsing container 2.

The lifting door 5 is configured to be movable in a motorized manner, for which purpose a drive device 9 is provided which, in the embodiment shown, has a pneumatic drive 10 and a deflection roller 11 over which a tension unit 12 in the form of a cable is guided from the pneumatic drive 10.

The tension unit 12 is connected by its end portion remote from the drive to a tension rod 18 via a linkage 24. In turn, the tension rod is connected to the lifting door 5 via swivelling levers 19, said swivelling levers 19 being arranged such that they can each rotate about the swivel axis 25 on the inside of the door frame 6 of the lifting door 5, as shown in particular in the view according to FIG. 2.

At one end, the swivelling levers 19 are each arranged on the tension rod 18 such that they can swivel about the rotational axis 26 and at the other end, they are arranged on a clamping device 17 in the form of a clamping strip such that they can swivel about the rotational axis 27. In this respect, the clamping device 17 is mounted inside a guide 16 in the direction of movement 14. A stop 30 is preferably provided which restricts the swivelling of the swivelling lever 19 and in this respect the stop 30 is arranged in particular on the clamping device 17. The clamping device 17 and the lifting door 5 are spring-preloaded with the interposition of tension springs 28, as can be seen in particular from the schematic diagram according to FIG. 3. In this respect, the lifting door 5 and the clamping device 17 are supported with respect to the common abutment 15, as can also be seen from the view according to FIG. 3.

Figure 3:
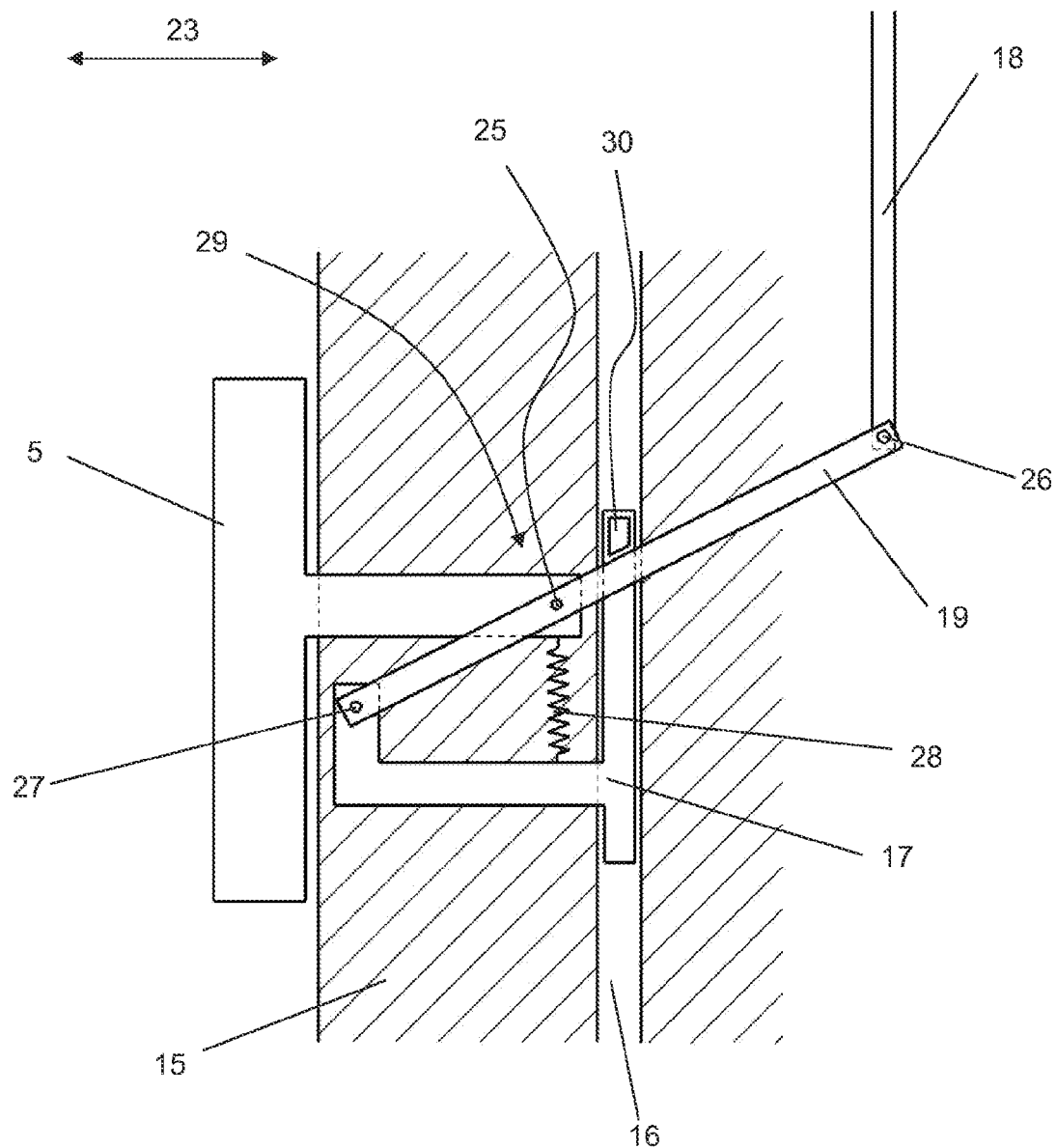
FIG. 3 is a schematic view of the operating principle according to the embodiment of the invention.

The mode of operation of the embodiment according to the invention can be seen in particular from the illustration of the operating principle according to FIG. 3.

If, during intended use, the lifting door 5 is to be raised, a tensile force is introduced into the cable acting as the tension unit 12 by the pneumatic drive 10, as a result of which force is introduced into the tension rod 18. Due to this force introduction, the swivelling levers 19 rotate and the lifting door 5 is pressed away from the seal 21 or the holder 22 for the seal 21 in the direction of movement 23 as a result of the clamping device 17 resting on the limit of the guide 16. Force is also introduced into the lifting door 5 via the swivelling levers 19, so that the lifting door moves upwards in the elevation direction. The springs 28 arranged between the lifting door 5 and the clamping device 17 are tensioned as a result of the displacement movement, initiated by the swivelling levers 19, of the clamping device 17.

If the drive device 9 should then fail, whether the drive 10 fails, the deflection roller 11 breaks, the tension unit 12 tears or a similar defect occurs which results in the inactivation of the lever arrangement 29, the lifting door 5 and the clamping device 17 are moved towards one another in the direction of movement 23 due to the spring force acting thereon and they are applied against the common abutment 15. Consequently, a friction locking is produced, resulting in the door 5 being braked and arrested. Therefore, even if the drive device 9 is defective, the lifting door 5 is reliably prevented from falling down.

The clamping device 17 is guided on both sides inside the guide 16, i.e. the clamping device 17 transmits horizontal forces in both directions, as a result of which it can press the lifting door 5 onto the seal 21 and, vice versa, can raise the lifting door off the seal 22. The tension springs 28 are preferably configured such that during the lifting procedure, they are compressed by the weight of the lifting door 5 and on the other hand during a failure, for example of the tension unit 12, they press the lifting door 5 directly against the seal 21, which then results in the automatic locking The spring force induced by the tension springs 28 is ideally just under the weight force of the lifting door 5.

For the automatic locking described above, the angle between the swivelling levers 19 and the frictional surface normals is smaller than the acute angle in the triangle consisting of normal force, frictional force and resulting force.

In addition to tension springs in vertical, horizontal or diagonal directions, compression springs in different directions or leg springs which introduce a torque into the swivelling levers are also conceivable.

If the seal 21 is configured as an inflatable seal, it is furthermore important in respect of the component dimensions that the horizontal forces arising during inflation of the seal 21 cannot push the lifting door 5 away. Here as well, an angle which is as acute as possible between the swivelling levers 19 and the surface normals should be selected.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

1 automatic rinsing machine
2 rinsing container
3 rinsing chamber
4 rinsing chamber opening
5 lifting door
6 door frame
7 outer pane
8 inner pane
9 drive device
10 pneumatic drive
11 deflection roller
12 tension unit
13 lever arrangement
14 direction of movement (elevation direction)
15 abutment
16 guide
17 clamping device
18 tension rod
19 swivelling lever
20 profile frame
21 seal
22 holding strip
23 direction of movement (vertical direction)
24 linkage
25 swivel axis
26 rotational axis
27 rotational axis
28 tension spring
29 lever arrangement
30 stop

What is claimed is:

1. An automatic rinsing machine, comprising:
   a rinsing container that includes a lifting door and a rinsing chamber with a rinsing chamber opening configured to be closed in a fluid-tight manner by the lifting door;
   a drive device configured to displace the lifting door, the drive device including a load-bearing tension unit;
   a tension rod connected to the tension unit; and
   a lever arrangement including a clamping device configured. to be guided in parallel with a direction of movement of the lifting door, and including a swivelling lever, the swivelling lever being rotatably connected to the lifting door at a swivel axis, one end of the swivelling lever rotatably connected to the tension rod at a first rotational axis and the other end of the swivelling lever being rotatably connected to the clamping device at a second rotational axis,
   wherein the lifting door and the clamping device are supported under spring preload with respect to a common abutment.

2. The automatic rinsing machine of claim 1, wherein the clamping device is a clamping strip arranged in a vertically extending guide.

3. The automatic rinsing machine of claim 1, wherein the tension rod is configured to be guided in parallel with the clamping device.

4. The automatic rinsing machine of claim 3, wherein the lifting door includes a door frame that is configured to support the swivelling lever such that it can rotate thereon.

5. The automatic rinsing machine of claim 3, further comprising a stop configured to restrict a swivelling movement of the swivelling lever.

6. The automatic rinsing machine of claim 4, wherein the swivelling lever is one of four swivelling levers, each of which is provided on a side of the door frame.

7. The automatic rinsing machine according to claim 1, further comprising a seal arranged between the common abutment and the lifting door.

8. The automatic rinsing machine according to claim 1, wherein the rinsing container is part of an automatic disinfection unit or an endoscope rinsing machine.

* * * * *